United States Patent [19]

Maeda et al.

[11] Patent Number: 5,162,556
[45] Date of Patent: Nov. 10, 1992

[54] ORGANIC GOLD COMPOUNDS AND METHOD OF PREPARING THE SAME

[75] Inventors: Koichi Maeda; Hideki Takamatsu; Gozyo Sakata; Takeshi Mita, all of Funabashi, Japan

[73] Assignee: Nissan Chemical Industries, Ltd., Tokyo, Japan

[21] Appl. No.: 615,405

[22] Filed: Nov. 19, 1990

[30] Foreign Application Priority Data

Nov. 30, 1989 [JP] Japan .................. 1-312135

[51] Int. Cl.$^5$ .................................. C07F 1/12
[52] U.S. Cl. ......................... 556/113; 556/110
[58] Field of Search .................. 556/110, 113

[56] References Cited

U.S. PATENT DOCUMENTS

| | | | |
|---|---|---|---|
| 2,490,399 | 12/1949 | Ballard | 556/113 |
| 2,984,575 | 5/1961 | Fitch | 106/1 |
| 2,994,614 | 8/1961 | Fitch | 556/113 |
| 3,163,665 | 12/1964 | Fitch | 260/430 |
| 3,245,809 | 4/1966 | Fitch | 556/113 |
| 3,268,568 | 8/1966 | Fitch | 260/430 |
| 3,661,959 | 5/1972 | Vaughan | 260/430 |

FOREIGN PATENT DOCUMENTS 621886 8/1961 Belgium .

*Primary Examiner*—Jose G. Dees
*Assistant Examiner*—Porfirio Nazario
*Attorney, Agent, or Firm*—Oliff & Berridge

[57] ABSTRACT

An auric compound such as a halogenoauric acid is reacted with a mercaptan of a formula:

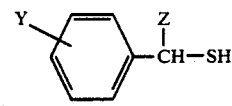

whereupon the proportion of the mercaptan is from 2.70 to 2.99 mols per mol of the auric compound, to prepare an organic gold compound of a formula:

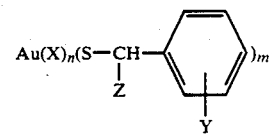

wherein X is a halogen atom, Y and Z are independently a hydrogen atom or a hydrocarbon group having from 1 to 18 carbon atoms, n is a number of from 0.01 to 0.30, m is a number of from 0.7 to 0.99, and the total of n and m is from 0.8 to 1.2. The organic gold compound has a high solubility in organic solvent such as terpineol.

17 Claims, No Drawings

ORGANIC GOLD COMPOUNDS AND METHOD OF PREPARING THE SAME

BACKGROUND OF THE INVENTION

1. Field of the Invention

The present invention relates to novel organic gold compounds and, more precisely, to those used for forming a metal gold by pyrolysis.

Specifically, the organic gold compounds of the present invention have such an improved property that show a high solubility in terpene alcohol solvents such as terpineol and in other solvents with an excellent stability of the resulting solution for a long period of time. A paste composition containing the compound in a form of solution may be used for forming a thin metal gold layer or film on a substrate.

2. Prior Art Description

Various organic gold compounds are known.

For instance, JP-B-37-2955 discloses gold tertiary alkylmercaptides; JP-B-40-22468 discloses gold secondary alkylmercaptides; and JP-B-41-18357 discloses gold arylmercaptides. (The term "JP-B" as used herein means an "examined Japanese patent publication.)

The above-mentioned conventional compounds are all represented by a formula (2):

Au—SR (2)

where Au represents a monovalent gold atom; and R represents a hydrocarbon group.

The known compounds are obtained by reacting a halogenoauric acid and a mercaptan in a proportion of 3 mols or more of mercaptan to mol of halogenoauric acid; or by reacting a compound of a formula (3):

where Au represents a monovalent gold atom, X represents a halogen atom, R represents a hydrocarbon group, and AuX is bonded to the sulfur atom by coordination bond, and a mercaptan in a proportion of one mol or more of mercaptan to mol of compound of formula (3).

The above-mentioned known compounds have a low solubility in low-polar organic solvents, such as terpineol, which are usually used as a vehicle of ink for screen-printing. In fact, they are substantially insoluble in such low-polar organic solvents at room temperature and they may only slightly be dissolved therein only under heat.

Therefore, it is impossible to obtain a paste of such compounds in high concentration, and the gold content in a paste containing the compound is limited in a low level and the thickness of the gold film to be formed therefrom is also limited. Additionally, selection of additives to be used for elevating the printability and adhesiveness between the gold film and the substrate as well as the amount of such additives is extremely limited.

SUMMARY OF THE INVENTION

The object of the present invention is to provide novel organic compounds, which have a high solubility in various solvents of not only terpene alcohol solvents such as terpineol, but also aromatic solvents such as toluene, halogenated hydrocarbon solvents such as methylene chloride, ketone solvents such as methyl ethyl ketone, ester solvents such as ethyl acetate, and ether solvents such as tetrahydrofuran, and which may stably maintain the solution of themselves as dissolved in such solvents for a long period of time.

Specifically, the present invention provides a novel organic gold compound which is composed of a gold atom, a halogen atom as bonding to the gold atom, and a mercapto group of formula

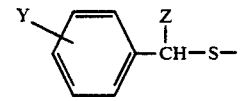

where Y and Z independently represent a hydrogen atom or a hydrocarbon group having from 1 to 18 carbon atoms, and Y and Z may be same as or different from each other, the proportion of the bonding halogen atom being from 0.01 mol to 0.30 mol to mol of the gold atom and that of the mercapto group being from 0.70 mol to 0.99 mol thereto, and the total amount of the bonding halogen atom and the mercapto group being within the range of from 0.8 mol to 1.2 mols to mol of the gold atom.

DETAILED DESCRIPTION OF THE INVENTION

Preferred examples of the bonding halogen atom in the compounds of the present invention include chlorine atom and bromine atom; and preferred examples of the mercapto group therein include benzylmercapto group, p-methylbenzylmercapto group, o-methylbenzylmercapto group, p-ethylbenzylmercapto group, p-normal-propylbenzylmercapto group, p-isopropylbenzylmercapto group, p-normal-butylbenzylmercapto group, p-isobutylbenzylmercapto group, p-tert-butylbenzylmercapto group, p-dodecylbenzylmercapto group, p-octadecylbenzylmercapto group, alpha-methylbenzylmercapto group, alpha-ethylbenzylmercapto group, alpha-methyl-p-methylbenzylmercapto group, alpha-ethyl-p-methylbenzylmercapto group, alpha-methyl-p-ethylbenzylmercapto group, alpha-methyl-p-normal-propylbenzylmercapto group, alpha-methyl-p-isopropylbenzylmercapto group, alpha-methyl-p-normal-butylbenzylmercapto group, alpha-methyl-p-isobutylbenzylmercapto group, alpha-methyl-p-tert-butylbenzylmercapto group, p-vinylbenzylmercapto group, p-cyclohexylbenzylmercapto group, p-phenylbenzylmercapto group, p-tolylbenzylmercapto group, p-xylylbenzylmercapto group and p-benzylbenzylmercapto group.

As mercapto group, one of the formula in which Z represents a hydrogen atom, a methyl group or an ethyl group, is preferable.

Also as mercapto group, one of the formula in which Y represents a hydrogen atom, an alkyl or alkenyl group having from 1 to 4 carbon atoms, a cyclohexyl group, a phenyl group, a tolyl group, a xylyl group or a benzyl group, as bonding to the para-position of the benzene ring, is preferable.

Organic gold compounds of the present invention are prepared, for example, by reacting an auric compound, preferably a halogenoauric acid, and a mercaptan having the above-mentioned mercapto group, in a proportion of from 2.70 to 2.99 mols of mercaptan to mol of auric compound, preferably in the presence of an inert solvent and preferably at a temperature lower than the decomposition temperature of the product to be formed, more preferably at a temperature falling within the range of from 0° to 80° C.

As examples of the inert solvent, there are mentioned alcohol solvents such as methanol or ethanol, aromatic solvents such as benzene or toluene, ester solvents such as ethyl acetate, ether solvents such as tetrahydrofuran, halogenated hydrocarbon solvents such as chloroform or methylene chloride, aliphatic hydrocarbon solvents such as hexane or heptane, and water.

The amount of the inert solvent to be used in the reaction may be such that smooth stirring and easy temperature control are possible during reaction.

The reaction time is, though depending upon the reaction temperature, generally from 1 to 24 hours.

After the reaction, the solvent is removed out from the reaction system by filtration or distillation to give the intended organic gold compound of the invention.

If desired, by-products such as disulfides may be extracted out from the product with methanol or ethanol, to thereby purify the product with ease.

As another method of producing the novel organic gold compounds of the invention, an auric compound, preferably a halogenoauric acid, is reacted with a mercaptan having the above-mentioned mercapto group in a proportion of from 3.00 mols of mercaptan to mol of auric compound to complete formation of an aurous mercaptide of a formula:

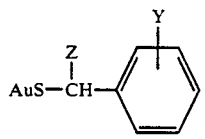

and the aurous mercaptide is, after isolated or not isolated, further reacted with an auric compound, preferably the above-mentioned halogenoauric acid, in a proportion of from 0.003 to 0.11 mol of auric compound to mol of the gold atom in the formed aurous mercaptide, to finally give an organic gold compound of the invention.

As still another method of producing the novel organic gold compounds of the invention, a compound of a formula (3):

$$R_2S \cdot AuX \quad (3)$$

where Au represents a monovalent gold atom, X represents a halogen atom, R represents a methyl, ethyl or butyl group, and AuX is bonded to the sulfur atom by coordination bond, is reacted with a mercaptan having the above-mentioned mercapto group in a proportion of from 0.70 to 0.99 mol of mercaptan to mol of compound of formula (3), to give an organic gold compound of the invention.

Also in the modified methods, the same inert solvent, reaction temperature and reaction time as those for the first method may preferably be employed to efficiently conduct the methods.

In accordance with the above-mentioned methods, gold compounds of the present invention, which comprise a gold atom, a halogen atom as bonding to the gold atom and the above-defined mercapto group and in which the proportion of the bonding halogen atom is from 0.01 mol to 0.30 mol to mol of gold atom and that of the mercapto group is from 0.70 mol to 0.99 mol thereto and the total of the bonding halogen atom and the mercapto group is within the range of from 0.8 mol to 1.2 mols to mol of gold atom, are obtained.

Organic gold compounds of the present invention have a high solubility in terpineol and are stable as a solution as dissolved in the solvent for several months without forming any precipitate in the solution.

Organic gold compounds of the present invention are amorphous (non-crystalline) by X-ray diffraction analysis.

Organic gold compounds of the present invention are stable and do not decompose when suspended in water. Additionally, when the compound is dissolved in an organic solvent such as toluene and then washed with a large amount of water, it liberates no halide ion therefrom.

There is no substantial difference in the result of elementary analysis between the purified organic gold compound of the present invention and the precipitates as obtained in the initial stage and in the last stage by the step of dissolving the compound in toluene followed by gradually adding methyl alcohol thereto to stepwise form precipitates in the resulting solution.

As opposed to the compounds illustrated in the above-mentioned Japanese patent publications, which have a low solubility of only several % in terpineol, organic gold compounds of the present invention have a high solubility in the above-mentioned organic solvents and give such a stable solutions as forming no precipitates for a long period of time. Though not theoretically clarified, the reason may be considered that the mercapto group of the above-mentioned formula has a good compatibility with the above-mentioned solvents and the bonding halogen atom participates in the coordination bond to give the soluble molecular structure.

Precisely, the organic gold compound of the present invention may be considered to be a coordination compound having a chemical structure where several gold mercaptides are positioned around the halogen atom via the gold atom by coordination bond and the gold atom and the halogen atom are surrounded by the solubilizable mercapto group.

AuX is immediately decomposed by water to liberate an X ion therefrom. Even in the absence of water, 3 mols of AuX are converted into 2 mols of metal Au and one mol of $AuX_3$. As opposed to them, the organic gold compound of the present invention does not liberate any halide ion even after it has been brought into contact with water. Therefore, it is obvious that the compound of the invention is neither a mere mixture of

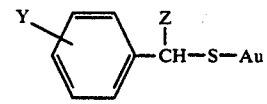

Additionally, in view of the fact that the above-mentioned fractional precipitates or the initial stage precipitate and the last stage precipitate have the same property, it is understood that the substance obtained by the method of the present invention is a single substance. Hence, the substance may be represented by a following chemical formula:

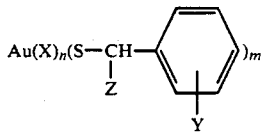

wherein Y and Z represent the same as that mentioned above and n represents a number of from 0.01 to 0.30 and m represents a number of from 0.7 to 0.99.

In preparing the organic gold compounds of the present invention, use of active solvents which react with gold or gold compounds should be evaded as the solvent would accelerate decomposing reaction or the like side-reactions.

Compounds having a molar ratio of the mercapto group to gold atom of being less than 0.70 are unfavorable, since they have a poor storage stability. On the other hand, those having the same molar ratio of being 1 (one) or more are also unfavorable, since they have an extremely low solubility.

Compounds having a molar ratio of the bonding halogen atom to gold atom of being more than 0.30 are unfavorable, since they have a poor storage stability. Those having the same molar ratio of being less than 0.01 are also unfavorable as having an extremely low solubility.

The following examples are intended to illustrate the present invention in more detail but not to limit it in any way.

EXAMPLE 1

10.55 g (58.5 mmol) of p-tert-butylbenzylmercaptan and 100 ml of methanol were put in a reaction flask to give a uniform solution, and 8.24 g (20 mmol) of chloroauric acid tetrahydrate ($HAuCl_4.4H_2O$) as dissolved in 10 ml of methanol was dropwise added thereto over a period of 30 minutes at room temperature with cooling with water and with stirring, whereupon the molar ratio of the mercaptan as fed into the flask to mol of Au was 2.93. Immediately the reaction system became a slurry. Afterwards, the reaction mixture was heated up to 50° C. and reacted at the said temperature for 2.5 hours. After cooled, the powdery product as formed was taken out by filtration at room temperature. Then, the product was washed with a large amount of methanol to remove disulfides therefrom and thereafter dried at 40° C. under reduced pressure to obtain 7.32 g of an yellow powdery product. The recovery percentage of gold was 100%. The molar ratio of the elements on the basis of gold atom, as obtained from the elementary analysis of the product, was shown in Table 1 below.

Solubility Test:

0.5 g of terpineol was added to one gram of the product and allowed to stand at room temperature, whereupon the product completely dissolved in the solvent to give a transparent solution.

Stability Test:

The terpineol solution formed as above was stored at room temperature in the dark under light-shielded condition for one year. As a result, no change was admitted in the thus stored solution with forming no precipitate therein.

Hydrolysis Test:

The product was dissolved in toluene and was washed with a large amount of water by stirring, whereupon only a trace of chloride ion was confirmed in the aqueous layer. The result of elementary analysis of the powder as recovered after washing as well as the solubility of the powder was same as that of the powder before washed.

Fractional Precipitation Test:

4.0 g of the product was dissolved in 15 ml of toluene and 9 ml of methanol was gradually added to the resulting solution at room temperature with stirring to form a precipitate in the solution. The precipitate thus formed was filtered and dried to obtain about 1.2 g of a first precipitate.

Next, 10 ml of methanol was further added gradually to the filtrate as remained after filtrate of the first precipitate, at room temperature with stirring to again form a precipitate thereon. The precipitate thus formed was filtered out and dried to obtain about 1.5 g of a second precipitate. Next, the filtrate was as remained after filtration of the second precipitate was dried up under reduced pressure to obtain about 1.1 g of a powder.

The results of elementary analysis of the product not dissolved in toluene, the first precipitate, the second precipitate and the powder last obtained by drying under reduced pressure were all same.

EXAMPLE 2

The same process as in Example 1 was repeated, except that the amount of p-tert-butylbenzylmercaptan was varied to 10.28 g (57 mmol) whereupon the molar ratio of the mercaptan to mol of Au was 2.85, and 6.89 g of an yellow powdery product was obtained. The recovery percentage of gold was 99%. The molar ratio of the elements on the basis of gold atom, as obtained from the elementary from the elementary analysis of the product, was shown in Table 1 below.

The product was subjected to the same "solubility test", "stability test", "hydrolysis test" and "fractional precipitation test" as those in Example 1, and the same results as those in Example 1 were obtained.

EXAMPLE 3

The same process as in Example 1 was repeated, except that the amount of p-tert-butylbenzylmercaptan was varied to 10.82 g (60 mmol) whereupon the molar ratio of the mercaptan to mol of Au was 3.00, and a white slurry was obtained. Afterwards, 0.44 g (1.07 mmol) of chloroauric acid tetrahydrate ($HAuCl_4.4H_2O$) as dissolved in 2.5 ml of methanol was dropwise added to the white slurry over a period of 30 minutes at room temperature with cooling with water and with stirring, whereupon the molar ratio of the supplemented Au to Au in the product before the supplement was 0.053. Next, the reaction mixture was heated up to 50° C. and reacted at the said temperature for 1.5 hours. After cooled, the powdery product as formed at room temperature was taken out by filtration and then washed with a large amount of methanol to remove disulfides therefrom. After dried at 40° C. under reduced pressure, 6.94 g of an yellow powdery product was obtained. The recovery percentage of gold was 98%. The molar ratio of the elements on the basis of gold atom, as obtained from the elementary analysis of the product, was shown in Table 1 below.

The product was subjected to the same "solubility test", "stability test", "hydrolysis" and "fractional precipitation test" as those in Example 1, and the same results as those in Example 1 were obtained.

COMPARATIVE EXAMPLE 1

The same process as in Example 1 was repeated, except that the amount of p-tert-butylbenzylmercaptan was varied to 10.82 g (60 mmol) whereupon the molar ratio of the mercaptan to mol of Au was 3.00, and 7.54 g of a white powdery product was obtained. The recovery percentage of gold was 100%. The molar ratio of the elements on the basis of gold atom, as obtained from the elementary analysis of the product, was shown in Table 1 below.

The product was subjected to the same "solubility test" as that in Example 1, but it did not dissolve at all. Even after it was heated up to about 70° C. in the solvent, only a trace of the compound could be admitted to be dissolved therein.

COMPARATIVE EXAMPLE 2

The same process as in Example 1 was repeated, except that the amount of p-tert-butylbenzylmercaptan was varied to 9.56 g (53 mmol), whereupon the molar ratio of the mercaptan to mol of Au was 2.65, and 6.25 g of a dark yellow powder product was obtained. The recovery percentage of gold was 95%. The molar ratio of the elements on the basis of gold atom, as obtained from the elementary analysis of the product, was shown in Table 1 below.

The product was subjected to the same "stability test" as that in Example 1, but a large amount of black precipitates precipitated after about 5 hours.

EXAMPLE 4

7.54 g of the white product as obtained in Comparative Example 1 and 100 ml of methanol were put in a reaction flask to form a slurry, and 0.44 g (1.07 mmol) of chloroauric acid tetrahydrate ($HAuCl_4 \cdot 4H_2O$) as dissolved in 2.5 ml of methanol was dropwise added thereto over a period of 30 minutes at room temperature with cooling with water and with stirring, whereupon the molar ratio of Au in the chloroauric acid as fed to Au in the white product as fed was 0.053. Next, the reaction mixture was heated up to 50° C. and reacted at the said temperature for 1.5 hours. After cooled, the powdery product as formed at room temperature was taken out by filtration and then washed with a large amount of methanol. After dried at 40° C. under reduced pressure, 7.39 g of an yellow powdery product was obtained. The recovery percentage of gold was 98%. The molar ratio of the elements on the basis of gold atom, as obtained from the elementary analysis of the product, was shown in Table 1 below.

The product was subjected to the same "solubility test", "stability test", "hydrolysis test" and "fractional precipitation test" as those in Example 1, and the same results as those in Example 1 were obtained.

TABLE 1

| Group | No. | Au | C | H | S | Cl | (S + Cl) |
|---|---|---|---|---|---|---|---|
| Example | 1 | 1 | 10.2 | 14.0 | 0.93 | 0.07 | 1.00 |
|  | 2 | 1 | 9.0 | 12.2 | 0.81 | 0.15 | 0.96 |
|  | 3 | 1 | 8.3 | 11.4 | 0.75 | 0.10 | 0.85 |
|  | 4 | 1 | 9.3 | 12.5 | 0.85 | 0.26 | 1.11 |
| Comparative | 1 | 1 | 10.8 | 15.0 | 1.01 | 0.005 | 1.02 |
| Example | 2 | 1 | 7.4 | 10.1 | 0.66 | 0.35 | 1.01 |

(Data of C, H, S, Cl and (S + Cl) in Table 1 above indicate mols of the respective elements per mol of gold atom, based on the result of elementary analysis of the product.)

It is understood that all the molar values of C, H and S of the above-mentioned results correspond to the calculated molar values of C, H and S of p-tert-butylbenzylmercapto group.

In the product of Comparative Example 1, the molar ratio of the mercapto group to gold atom is more than 1 and the molar ratio of the bonding halogen atom to gold atom is less than 0.01. Accordingly, the product has an extremely low solubility.

In the product of Comparative Example 2, the molar ratio of the mercapto group to gold atom is less than 0.70 and the molar ratio of the bonding halogen atom to gold atom is more than 0.30. Accordingly, the product has an extremely low storage stability.

When organic gold compounds of the present invention are pyrolyzed, a metal gold is formed. Organic gold compounds of the present invention have a high solubility in not only low-polar terpene alcohol solvent, such as terpineol, which are frequently used as a solvent in screen-printing, but also aromatic solvents such as toluene, halogenated hydrocarbon solvents such as methylene chloride, ketone solvents such as methyl ethyl ketone, ester solvents such as ethyl acetate or ether solvents such as tetrahydrofuran. Additionally, they are so improved that they may stably maintain the solution condition of themselves as dissolved in such solvents for a long period of time. A paste composition containing such an organic gold compound of the present invention may be used for decorating a substrate by forming a thin metal gold film thereon or for forming an electroconductive circuit of a thin metal gold film on a substrate.

Where the compound of the present invention is used as a component of a gold paste composition, the gold content in the paste may freely be controlled to fall within a broad range of from a high concentration to a low concentration. Additionally, the kind of the additives to be used for the purpose of improving the printability of the paste onto a substrate and the adhesiveness between the gold film to be formed from the paste and the substrate as well as the amount of such additives is not limited so much. Accordingly, when the paste is printed on a substrate or when a substrate is dipped in the paste and then fired, a uniform metal gold film may be formed on the substrate, having a high adhesiveness to the substrate. In the case, the thickness of the gold film to be formed may freely be controlled do some degree.

While the invention has been described in detail and with reference to specific embodiments thereof, it will be apparent to one skilled in the art that various changes and modifications can be made therein without departing from the spirit and scope thereof.

What is claimed is:

1. An organic gold compound of a formula:

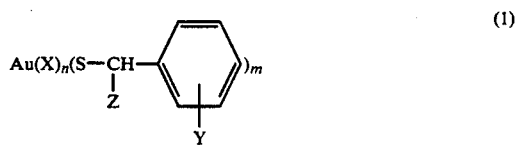

(1)

wherein Y and Z independently represent a hydrogen atom or a hydrocarbon group having from 1 to 18 carbon atoms, and X is halogen, wherein n equals 0.01 to 0.30 and m equals 0.7 to 0.99, and the total amount of the bonding halogen atom and the mercapto group being within the range from 0.8 mol to 1.2 mols to mol of the gold atom.

2. An organic gold compound as claimed in claim 1, wherein the bonding halogen atom is Cl or Br.

3. An organic gold compound as claimed in claim 1, wherein Z in the formula (1) is a hydrogen atom, a methyl group or an ethyl group.

4. An organic gold compound as claimed in claim 1, wherein Y in the formula (1) is a hydrogen atom, an alkyl or alkenyl group having from 1 to 4 carbon atoms, a cyclohexyl group, a phenyl group, a tolyl group, a xylyl group or a benzyl group, as bonding to the para-position of the benzene skeleton.

5. An organic gold compound as claimed in claim 1, wherein Y in the formula (1) is a hydrogen atom, a methyl group or an ethyl group, as bonding to the ortho-position of the benzene skeleton.

6. An organic gold compound as claimed in claim 1, wherein the mercapto group is a benzylmercapto group, p-methylbenzylmercapto group, o-methylbenzylmercapto group, p-ethylbenzylmercapto group, p-normal-propylbenzylmercapto group, p-isopropyl-benzylmercapto group, p-normal-butylbenzylmercapto group, p-isobutylbenzylmercapto group, p-tert-butylbenzylmercapto group, p-dodecylbenzylmercapto group, p-octadecylbenzylmercapto group, alpha-methylbenzylmercapto group, alpha-ethylbenzylmercapto group, alpha-methyl-p-methylbenzylmercapto group, alpha-ethyl-p-methylbenzylmercapto group, alpha-methyl-p-ethylbenzyl-mercapto group, alpha-methyl-p-normal-propylbenzylmercapto group, alpha-methyl-p-isopropylbenzylmercapto group, alpha-methyl-p-normal-butylbenzylmercapto group, alpha-methyl-p-isobutylbenzylmercapto group, alpha-methyl-p-tert-butylbenzylmercapto group, p-vinylbenzylmercapto group, p-cyclohexylbenzylmercapto group, p-phenylbenzylmercapto group, p-tolylbenzylmercapto group, p-xylylbenzylmercapto group and p-benzylbenzylmercapto group.

7. The organic gold compound of claim 1, wherein n equals 0.070–0.26.

8. The organic gold compound of claim 1, wherein m equals 0.75–0.93.

9. The organic gold compound of claim 1, wherein n equals 0.070–0.26 and m equals 0.75–0.93.

10. A method of preparing an organic gold compound of a formula:

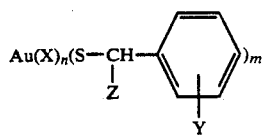
(1)

wherein Y and Z independently represent a halogen atom or a hydrocarbon group having from 1 to 18 carbon atoms, and X is a halogen, wherein n equals 0.01 to 0.30 and m equals 0.70 to 0.99, and the total amount of the bonding halogen atom and the mercapto group being within the range of from 0.8 mol to 1.2 mols to mol of the gold atom; wherein (A) a halogenoauric acid is reacted with a mercaptan of a formula:

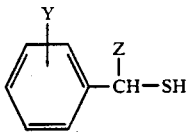

wherein Y and Z have the same meanings as mentioned above, in an inert solvent at 0° to 80° C., the proportion of the mercaptan being from 2.70 to 2.99 mols to mol of the halogenoauric acid; or (B) a halogenoauric acid is reacted with a mercaptide of a formula:

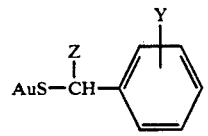

wherein Y and Z have the same meanings as above, in an inert solvent at 0° to 80° C., the proportion of the mercaptide being from 9.09 to 333.33 mols to mol of the halogenoauric acid; or (C) an aurous compound of a formula:

$$R_2S \cdot AuX$$

wherein X represents a halogen atom, and R represents an alkyl group having from 1 to 4 carbon atoms, is reacted with a mercaptan of the formula:

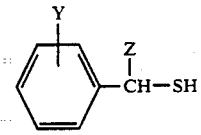

wherein Y and Z have the same meanings as mentioned above, in an inert solvent at 0° to 80° C., the proportion of the mercaptan being from 0.70 to 0.99 mols to mol of the aurous compound.

11. A method of preparing an organic gold compound as claimed in claim 10, wherein the halogenoauric acid is chloroauric acid or bromoauric acid.

12. A method of preparing an organic gold compound as claimed in claim 10, wherein the inert solvent is selected from the group consisting of water, alcohols, esters, ethers, aliphatic hydrocarbons, aromatic hydrocarbons and halogenated hydrocarbons.

13. A method of preparing an organic gold compound as claimed in claim 10, wherein X in the aurous compound is Cl or Br, and R therein is a methyl group, an ethyl group or a butyl group.

14. A method of preparing an organic gold compound as claimed in claim 10, wherein Z in the formulae is a hydrogen atom, a methyl group or an ethyl group.

15. A method of preparing an organic gold compound as claimed in claim 10, wherein Y in the formulae is a hydrogen atom, an alkyl or alkenyl group having from 1 to 4 carbon atoms, a cyclohexyl group, a phenyl group, a tolyl group, a xylyl group or a benzyl group, as bonding to the para-position of the benzene skeleton.

16. A method of preparing an organic gold compound as claimed in claim 10, wherein Y in the formulae is a hydrogen atom, a methyl group or an ethyl group, as bonding to the ortho-position of the benzene skeleton.

17. A method of preparing an organic gold compound as claimed in claim 10, wherein the mercapto group is a benzylmercapto group, p-methylbenzylmercapto group, o-methylbenzylmercapto group, p-ethylbenzylmercapto group, p-normal-propylbenzylmercapto group, p-isopropyl-benzylmercapto group, p-normal-butylbenzylmercapto group, p-isobutylbenzylmercapto group, p-tert-butylbenzylmercapto group, p-dodecylbenzylmercapto group, p-octadecylbenzylmercapto group, alpha-methylbenzylmercapto group, alpha-ethylbenzylmercapto group, alpha-methyl-p-methylbenzylmercapto group, alpha-ethyl-p-methylbenzylmercapto group, alpha-methyl-p-ethylbenzylmercapto group, alpha-methyl-p-normal-propylbenzylmercapto group, alpha-methyl-p-isopropylbenzylmercapto group, alpha-methyl-p-normal-butylbenzylmercapto group, alpha-methyl-p-isobutylbenzylmercapto group, alpha-methyl-p-tert-butylbenzylmercapto group, p-vinylbenzylmercapto group, p-cyclohexylbenzylmercapto group, p-phenylbenzylmercapto group, p-tolylbenzylmercapto group, p-xylylbenzylmercapto group and p-benzylbenzylmercapto group.

* * * * *